(12) United States Patent
Onobori

(10) Patent No.: US 12,329,362 B2
(45) Date of Patent: Jun. 17, 2025

(54) ILLUMINATION APPARATUS

(71) Applicant: HOYA CORPORATION, Tokyo (JP)

(72) Inventor: Kunihiko Onobori, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 499 days.

(21) Appl. No.: 17/792,245

(22) PCT Filed: Dec. 10, 2020

(86) PCT No.: PCT/IB2020/061726
§ 371 (c)(1),
(2) Date: Jul. 12, 2022

(87) PCT Pub. No.: WO2021/152382
PCT Pub. Date: Aug. 5, 2021

(65) Prior Publication Data
US 2023/0082243 A1    Mar. 16, 2023

(30) Foreign Application Priority Data
Jan. 27, 2020    (DE) ............... 10 2020 101 853.3

(51) Int. Cl.
*A61B 1/06* (2006.01)
*A61B 1/04* (2006.01)
*A61B 1/07* (2006.01)

(52) U.S. Cl.
CPC ............ *A61B 1/0653* (2013.01); *A61B 1/041* (2013.01); *A61B 1/0638* (2013.01);
(Continued)

(58) Field of Classification Search
CPC ................ A61B 1/0653; A61B 1/0655; A61B 1/0676; A61B 1/0684; A61B 1/0607; A61B 1/0638
See application file for complete search history.

(56) References Cited

U.S. PATENT DOCUMENTS

| | | | |
|---|---|---|---|
| 2008/0165307 A1 | 7/2008 | Adachi et al. | |
| 2011/0074942 A1* | 3/2011 | Endo | A61B 1/00186 348/E7.085 |
| 2011/0077465 A1* | 3/2011 | Mizuyoshi | A61B 1/0638 600/178 |

(Continued)

FOREIGN PATENT DOCUMENTS

| | | |
|---|---|---|
| CN | 108533970 A | 9/2018 |
| EP | 3095142 | 11/2016 |

(Continued)

OTHER PUBLICATIONS

International Search Report issued in International Bureau of WIPO Patent Application No. PCT/IB2020/061726, dated Feb. 10, 2021.
(Continued)

*Primary Examiner* — William N Harris
(74) *Attorney, Agent, or Firm* — GREENBLUM & BERNSTEIN, P.L.C.

(57) ABSTRACT

An illumination apparatus includes an exit layer including a phosphor; a plurality of first light sources and a plurality of second light sources; wherein, the first light sources and the second light sources are arranged in plural unit cells; the plurality of the first light sources is controllable separately from the plurality of the second light sources; the first and second light sources are arranged spaced apart from the exit layer; the phosphor converts at least a portion of the first lights into first converted lights; if the first and second light sources emit the first and second lights, respectively, on a line connecting corresponding positions of two adjacent unit cells of the plurality of unit cells projected on the exit layer, a variation of a total intensity of the respective lights is less than 20%.

10 Claims, 16 Drawing Sheets

(52) U.S. Cl.
CPC .......... *A61B 1/0655* (2022.02); *A61B 1/0676* (2013.01); *A61B 1/0684* (2013.01); *A61B 1/07* (2013.01)

(56) References Cited

U.S. PATENT DOCUMENTS

| | | | |
|---|---|---|---|
| 2012/0044713 | A1 | 2/2012 | Chiang et al. |
| 2013/0018242 | A1* | 1/2013 | Yamaguchi .......... A61B 1/0638 600/339 |
| 2016/0161067 | A1 | 6/2016 | Oepts et al. |
| 2016/0290573 | A1 | 10/2016 | Allen et al. |
| 2016/0295085 | A1 | 10/2016 | Aoyama |
| 2016/0320001 | A1 | 11/2016 | Soer et al. |
| 2023/0280001 | A1* | 9/2023 | Onobori .................... F21K 9/64 362/249.01 |

FOREIGN PATENT DOCUMENTS

| | | |
|---|---|---|
| JP | 2011-003594 | 1/2011 |
| JP | 2011-167442 | 9/2011 |
| JP | 2016-059402 | 4/2016 |
| JP | 2016-531432 | 10/2016 |
| JP | 2016-195684 | 11/2016 |
| JP | 2017-501580 | 1/2017 |
| JP | 2017-502493 | 1/2017 |
| JP | 2019-162165 A | 9/2019 |
| WO | 2019/159817 A1 | 8/2019 |

OTHER PUBLICATIONS

Notice of Reasons for Refusal issued in Japanese Patent Application No. 2022545924, dated Jun. 6, 2023, together with an English-language translation.

Decision to Grant a Patent issued in Japanese Patent Application No. 2022-545924, dated Oct. 3, 2023, together with an English-language translation.

First Office Action issued in Chinese Patent Application No. 202080097496.2, dated Feb. 11, 2024, together with an English-language translation.

* cited by examiner

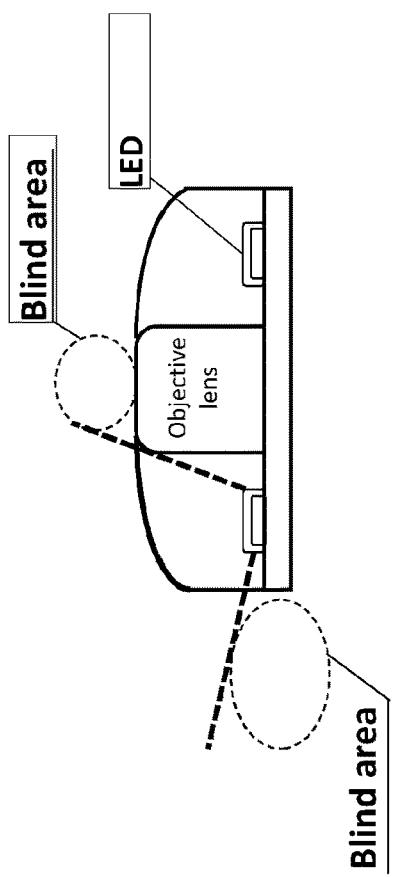
Fig. 2
Prior art
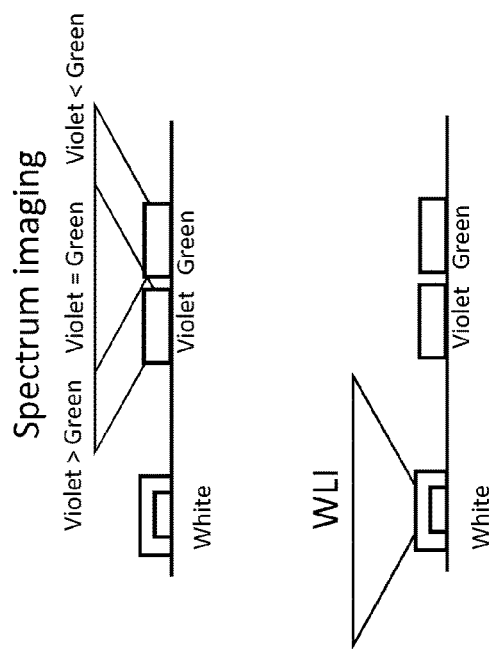
Fig. 1
Prior art
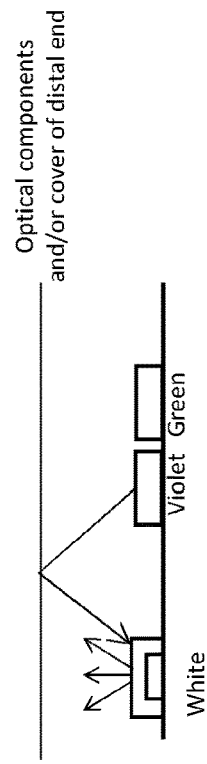

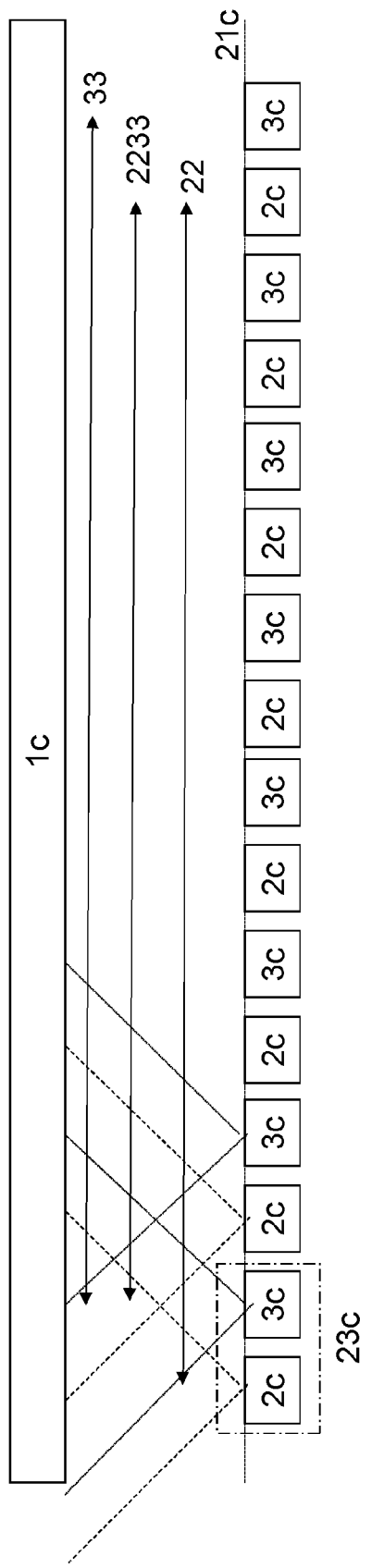

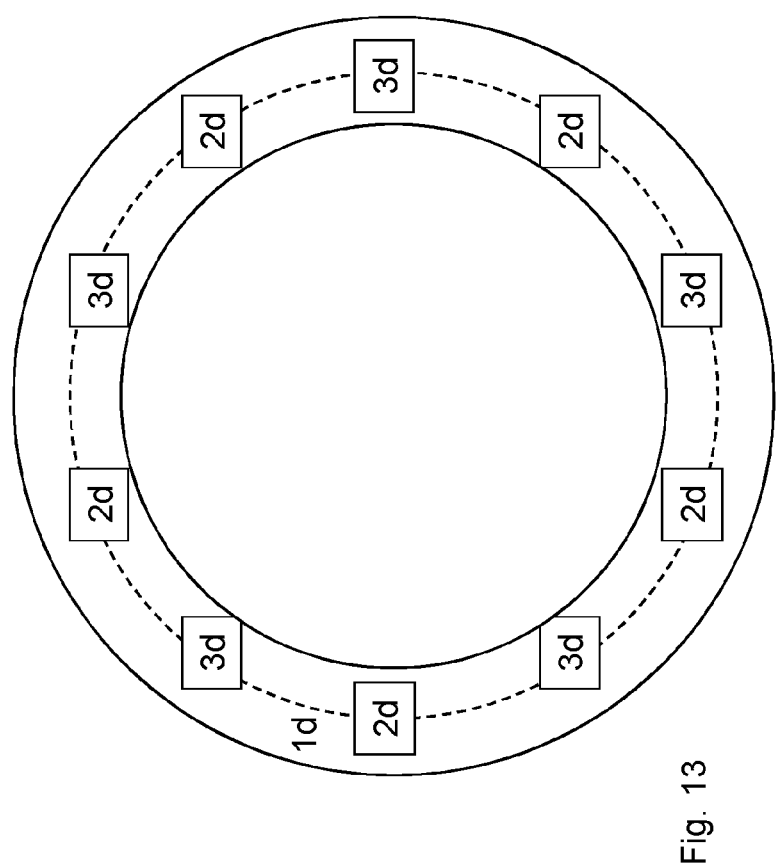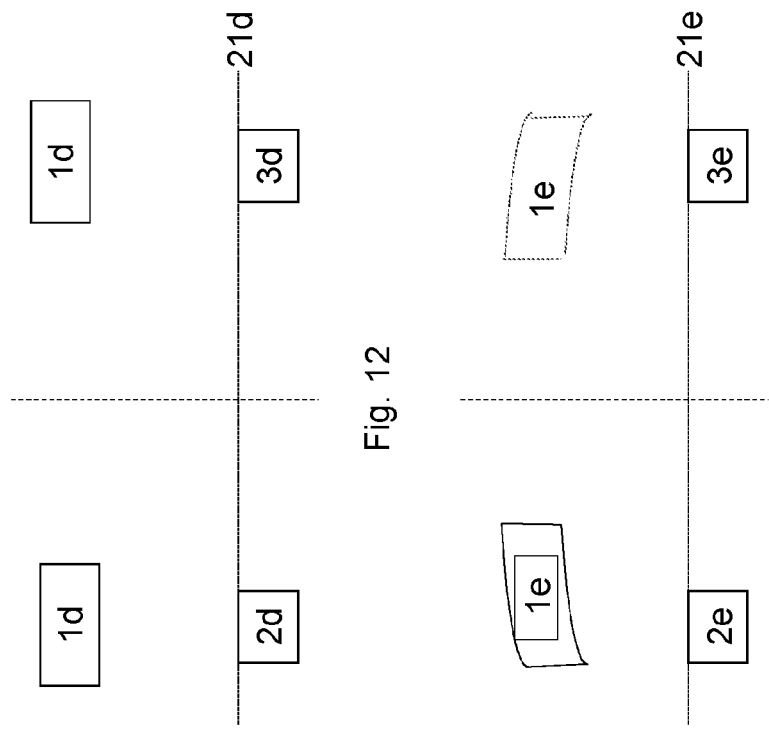

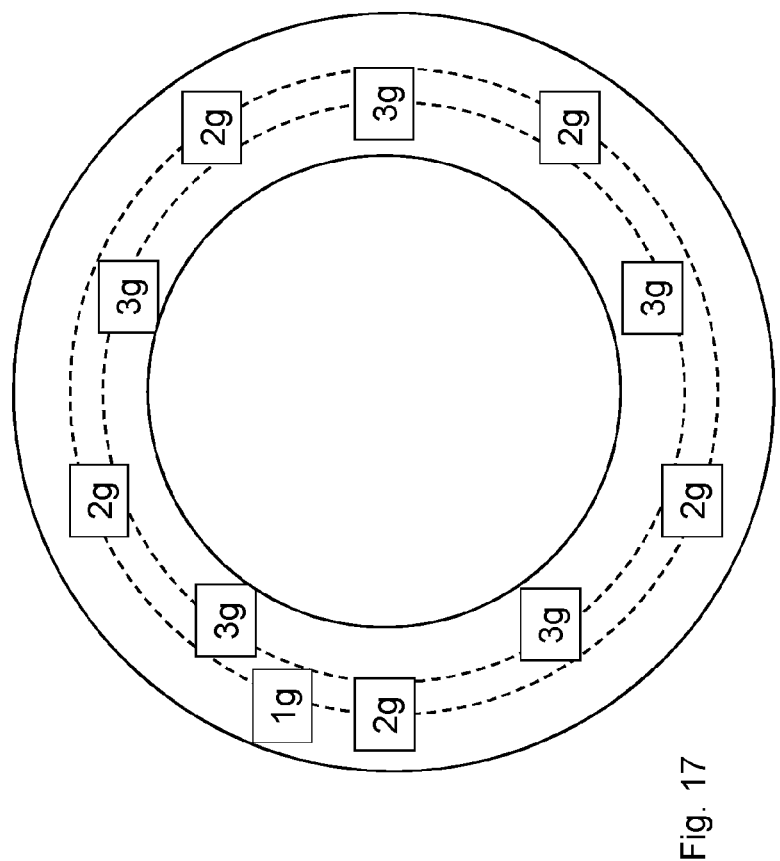
Fig. 17
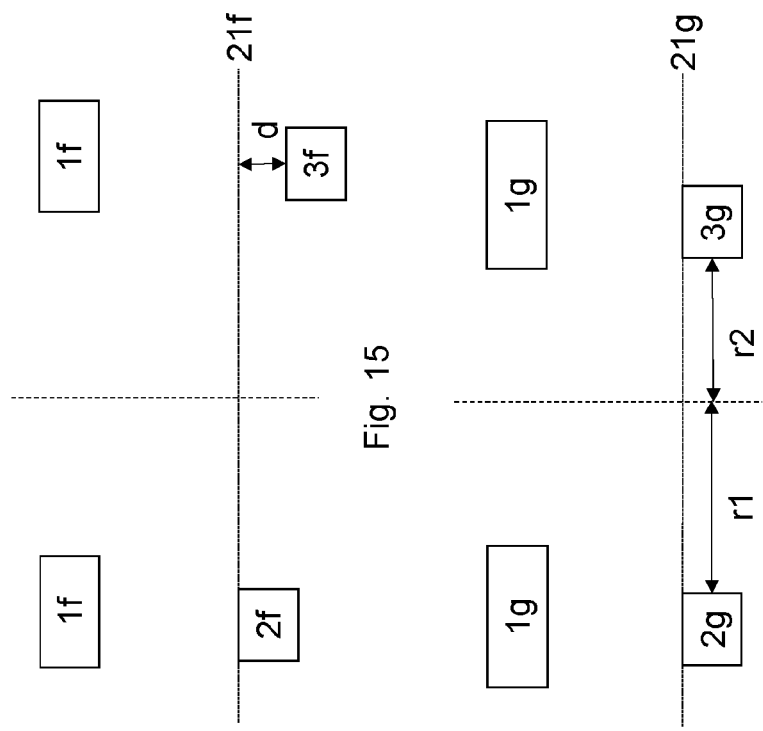
Fig. 15
Fig. 16

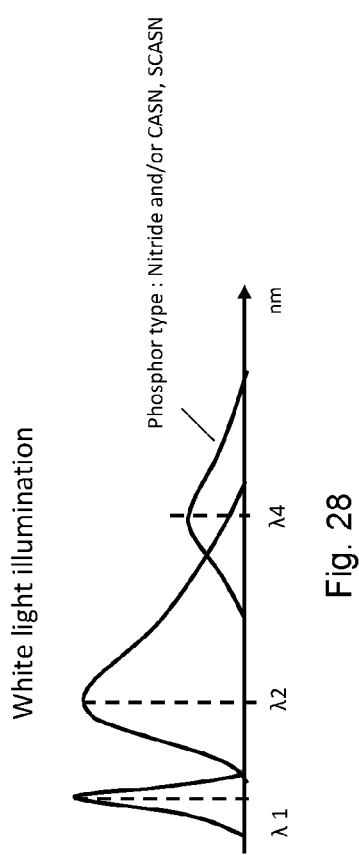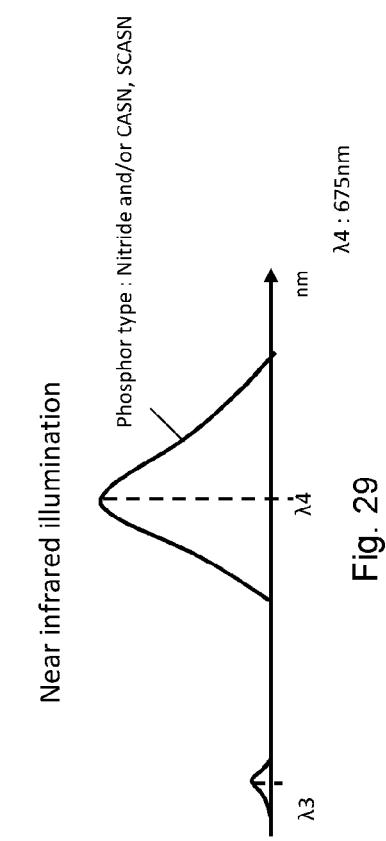

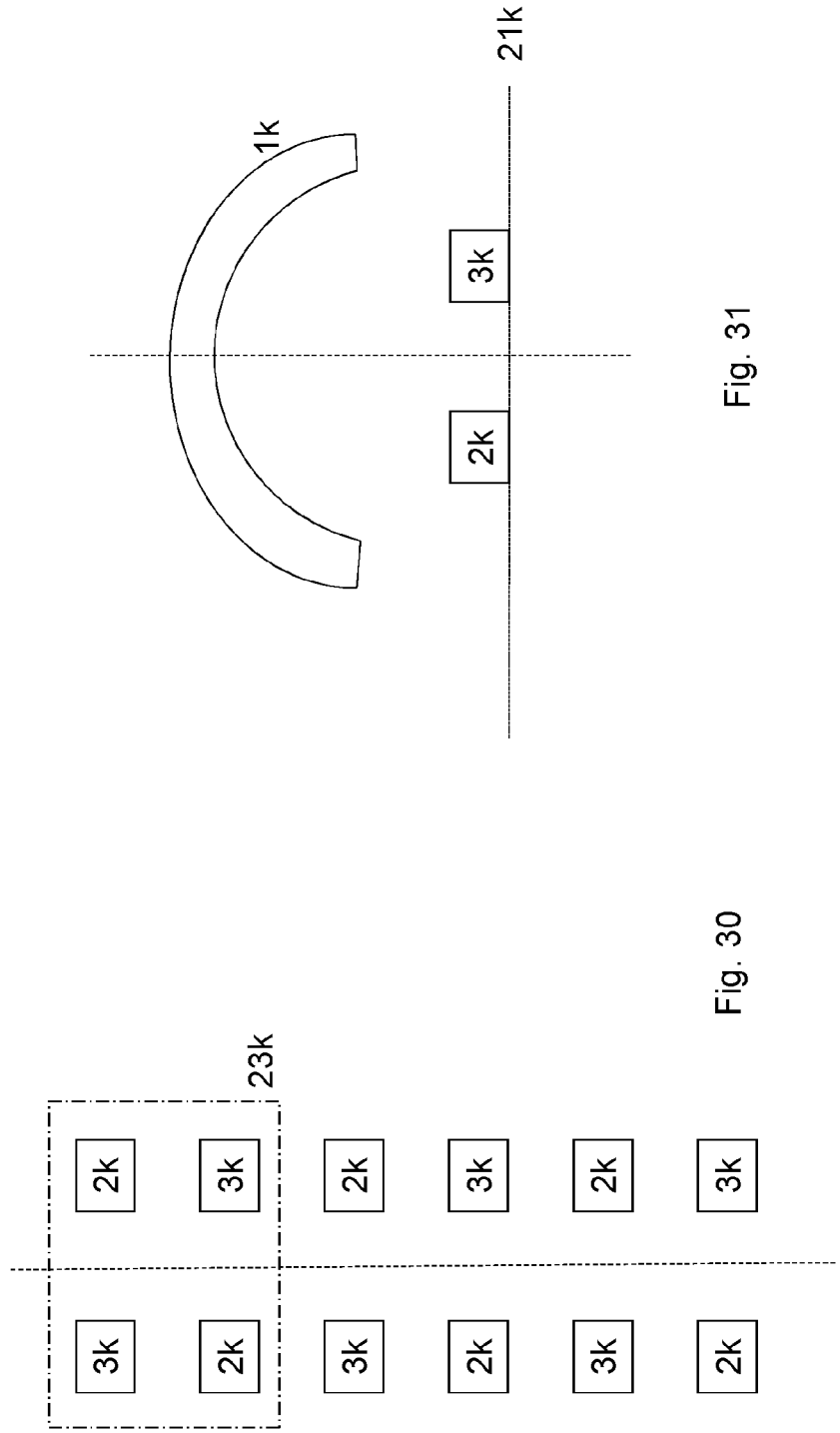

ILLUMINATION APPARATUS

FIELD OF THE INVENTION

The present invention relates to an illumination apparatus for illuminating an object with different spectra. In particular, it relates to an illumination apparatus, which is useful in the tip portion of an endoscope, in particular an endoscope comprising a wide field of view objective lens.

BACKGROUND OF THE INVENTION

Imaging with different colored light is known in the art. For example, there is white light imaging (WLI) and "spectrum imaging". In WLI, the object (such as a colon) is illuminated by white light. In contrast, in spectrum imaging, the object is illuminated with light having a spectral distribution different from that of white light. For example, spectrum imaging with a spectrum comprising substantially only violet and green light is known.

FIG. 1 shows an illumination system for an endoscope according to the prior art which allows both WLI and spectrum imaging. This illumination system comprises a white LED (here shown as a blue LED with the yellow phosphor covering the blue LED) and, separated from the white LED, a violet LED and a green LED. In spectrum imaging, only the violet and green LEDs emit light. Thus, the emitted light has a gradient from violet on the left side via green violet to green on the right side. In WLI, only the white LED emits light.

Such illumination system has several disadvantages: the relative intensity of the violet and green light varies with the position on the object. Furthermore, the illumination by the white light is at a different position on the object than the illumination by the violet and green LEDs. Thus, a doctor using the prior art endoscope cannot easily observe the same position under different illuminations. Still furthermore, quite some space is required to accommodate the 3 LEDs in the tip portion of the endoscope.

In another illumination system according to the prior art, as shown in FIG. 2, plural LEDs (such as white LEDs) are arranged around an objective lens. In such a configuration, the space immediately in front of the objective lens is a blind area because of the shadow of the objective lens. Furthermore, if the objective lens has a wide field of view in the order of 180° or even more, the illumination system does not illuminate the outer part of the field of view. Thus, an additional blind area exists on the outer side of the illumination system.

SUMMARY OF THE INVENTION

It is an object of the present invention to improve the prior art. Namely, according to an aspect of the present invention, there is provided an illumination system according to the independent claim. Further aspects of the invention provide a rigid tip of an endoscope, and an endoscope comprising the illumination system. Further details are set out in the respective dependent claims.

According to some embodiments of the invention, at least one of the following advantages may be achieved:
- the space required for the illumination apparatus enabling both WLI and spectrum illumination is reduced;
- the blind areas are reduced or even completely avoided;
- the configuration is easy to implement;
- depending on the needs, the light sources may be LEDs and/or emission ends of optical fibers;
- the color distribution is more homogeneous than according to the prior art;
- a doctor may easily observe a position under different illuminations.

Further advantages become apparent from the following detailed description.

It is to be understood that any of the above modifications and the examples described below can be applied singly or in combination to the respective aspects to which they refer, unless they are explicitly stated as excluding alternatives.

BRIEF DESCRIPTION OF THE DRAWINGS

Further details, features, objects, and advantages are apparent from the following detailed description of preferred embodiments of the invention, which is to be taken in conjunction with the appended drawings, wherein:

FIG. 1 shows an illumination system according to the prior art;

FIG. 2 shows an illumination system according to the prior art;

FIG. 11 shows a cross-section through an illumination apparatus according to some embodiments of the invention;

FIG. 12 shows a cross-section of an illumination apparatus according to some embodiments of the invention;

FIG. 13 shows a plan view on the illumination apparatus of FIG. 12;

FIG. 14 shows a cross-section to an illumination apparatus according to some embodiments of the invention;

FIG. 15 shows a cross-section through an illumination apparatus according to some embodiments of the invention;

FIG. 16 shows a cross-section through an illumination apparatus according to some embodiments of the invention;

FIG. 17 shows a plan view on the illumination apparatus according to FIG. 16;

FIG. 28 shows the emission spectrum of an illumination apparatus according to some embodiments of the invention used in WLI;

FIG. 29 shows the emission spectrum of an illumination apparatus according to some embodiments of the invention used in near infrared illumination.

FIG. 30 shows a plan view on an illumination apparatus according to some embodiments of the invention; and FIG. 31 shows a cross-section through an illumination apparatus according to FIG. 30.

DETAILED DESCRIPTION OF CERTAIN EMBODIMENTS

Herein below, certain embodiments of the present invention are described in detail as reference to the accompanying drawings, wherein the features of the embodiments can be freely combined with each other unless otherwise described. However, it is to be expressly understood that the description of certain embodiments is given by way of example only, and that it is by no means intended to be understood as limiting the invention to the disclosed details.

In the Figures, the same numerals designate corresponding components, which are distinguished by different letters. The Figures are schematic only. In particular, the sizes are not at scale. For example, the light sources (LEDs or emission ends of optical fibers) may be substantially a point.

Figure 3:
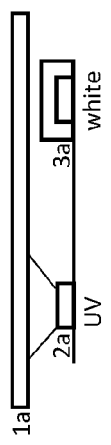
FIG. 3 shows a cross-section of a unit cell of an illumination apparatus according to some embodiments of the invention, used in spectrum illumination.

FIG. 3 shows a unit cell of an illumination apparatus according to some embodiments of the invention. The unit cell comprises a first LED 2a of a first type (such as a LED emitting UV light), and a second LED 3a, which emits a different spectrum, such as a white LED. Each of these LEDs is an example of a light source. The LEDs of the unit illuminate an exit layer 1a. A phosphor is arranged in the exit layer. The phosphor converts at least a portion of the light from the first LED (first light) into first converted light. In addition, the phosphor may convert at least a portion of the light from the second LED (second light) into second converted light. The first converted light has a different spectrum than the first light. The second converted light has a different spectrum than the second light.

Figure 4:
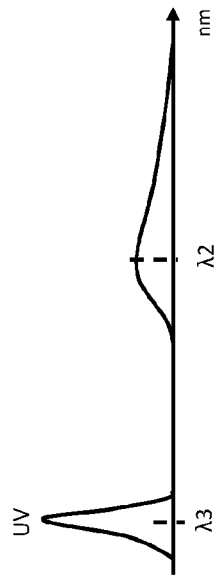
FIG. 4 shows an emission spectrum if the illumination apparatus of FIG. 3 is used in spectrum illumination.

For example, as shown in FIG. 4, in case of spectrum illumination, only the UV LED 2a illuminates the exit layer with light, while the white LED is switched off. In this case, the emission spectrum comprises violet or deep blue light (sometimes also called UV light) from the LED 2a around wavelength (peak wavelength) $\lambda 3$ (e.g. 400 to 430 nm), and green light from the conversion by the phosphor in the exit layer 1a (for example of a wavelength around $\lambda 2$: 520 to 580 nm).

In white light illumination, only the second LED 3a illuminates light on the exit layer 1a, while the first LED 2a is dark. In this case, the white LED is a phosphor covered blue LED which has an emission spectrum as shown by the dashed line in FIG. 6. That is, it has a high peak in the blue region ($\lambda 1$ about 440 to 460 nm) and a broad maximum in the green region around $\lambda 2$. Due to the conversion by the phosphor in the exit layer 1a, the intensity of the blue light around $\lambda 1$ is reduced and the broad maximum around $\lambda 2$ is enhanced and broadened. Thus, white light illumination is performed.

Figure 6:
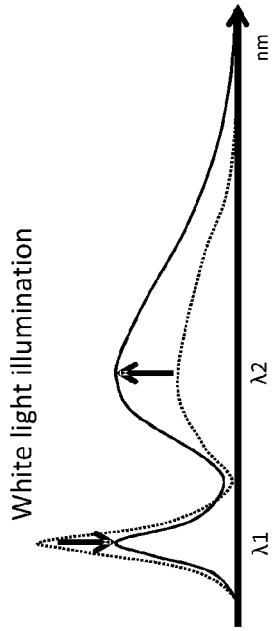
FIG. 6 shows the spectrum of emitted light if the illumination apparatus of FIG. 5 is used in WLI.

The spectra shown in FIGS. 4 and 6 are examples only. Other combinations of different types of LEDs combined with different types of phosphors fall under the scope of the present invention. Instead of a single type of phosphor, plural types of phosphor may be used in the exit layer. These different types of phosphors may be mixed or arranged in different layers.

Figure 5:
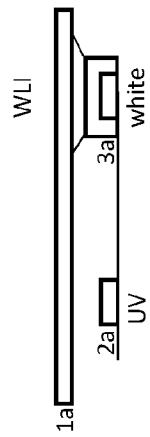
FIG. 5 shows the unit cell of the illumination apparatus according to FIG. 3 used in WLI.
Figure 8:
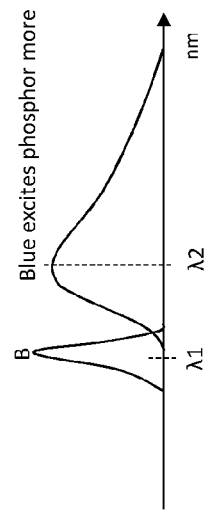
FIG. 8 shows the emission spectrum of the illumination apparatus of FIG. 7 used in spectrum illumination.

FIGS. 7 to 10 show another example of the units according to some embodiments of the invention, which correspond to FIGS. 3 to 6, except that the white LED 3a of FIGS. 3 and 5 is replaced by the blue LED 3b emitting light in the range of 440 to 460 nm. Since in this example the first LED 2b and the phosphor in the exit layer 1b are the same as in FIGS. 3 and 5, the spectrum in the case of spectrum illumination shown in FIG. 8 as the same as that shown in FIG. 4.

Figure 10:
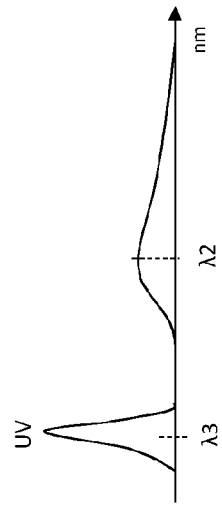
FIG. 10 shows the emission spectrum of the illumination apparatus of FIG. 9 used in WLI.
Figure 7:
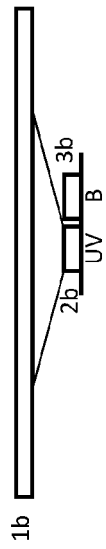
FIG. 7 shows a unit cell of another illumination apparatus according to some embodiments of the invention, used in spectrum illumination.
Figure 9:
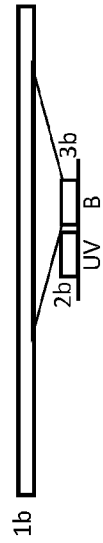
FIG. 9 shows the illumination apparatus of FIG. 7 used in WLI.

However, in case of white light illumination, the blue LED 3b excites the phosphor more than the white LED 3a of FIGS. 3 and 5. Therefore, the emission spectrum in case of white light illumination has a larger and broader peak around $\lambda 2$, as shown in FIG. 10.

FIG. 11 shows an illumination apparatus according to some embodiments of the invention. In the illumination apparatus of FIG. 11, there is an exit layer 1c, which has a bottom surface and a top surface. Light from the LEDs 2c and 3c is illuminated on the bottom surface, converted by the phosphor arranged in the exit layer, and the combined light of the remaining portions of the lights emitted from the LEDs 2c and 3c and of the converted lights is emitted from the top surface of the exit layer.

The illumination apparatus comprises plural LEDs 2c of the first type (first LEDs) and plural LEDs 3c of the second type (second LEDs). The first and second types of LEDs have different emission spectra. The LEDs are arranged in unit cells 23c, wherein each unit cell comprises at least one first LED and at least one second LED. In the example of FIG. 11, each unit cell 23c comprises one first LED 2c and one second LED 3c. The arrangement of the respective first and second LEDs is the same in all of the unit cells. For illustration, illumination cones of some of the LEDs are indicated in FIG. 11.

The illumination apparatus comprises plural unit cells. The unit cells are arranged periodically in a base plane 21c. The base plane 21c is a plane which results from connecting corresponding points of the unit cells. In the example of FIG. 11, the base plane 2c1 comprises the emission faces of the LEDs 2c and 3c.

All the first LEDs 2c and second LEDs 3c are spaced apart from the exit layer 1c. Thus, each of these LEDs can illuminate a quite large portion of the exit layer 1c comprising the phosphor. In particular, in the area 33 of the bottom surface of the exit layer 1c, each position of the bottom surface is illuminated by at least two of the LEDs 3c. Correspondingly, in the area 22 of the bottom layer, each position of the bottom layer is illuminated by at least two first LEDs 2c. Thus, in the areas 22 and 33, a relatively homogeneous illumination of the phosphor in the exit layer may be achieved for the illumination by the respective lights. In the overlapping area 2233 of the areas 22 and 33, illumination by both the first LEDs and the second LEDs is relatively homogeneous.

The term "relatively homogeneous" means that the total intensity of the respective lights illuminating the bottom surface of the exit layer does not vary by more than 20%. It is preferred that the variation is less than 10%, or even less than 5%. It is preferred that the illumination of the bottom surface of the exit layer is substantially homogeneous over the whole surface. However, according to some embodiments, it is sufficient that the illumination intensity is substantially homogeneous over a line on the bottom surface, which is obtained by projecting corresponding points in two adjacent unit cells on the bottom surface. The projection may be perpendicular to the base plane (base layer) if the base layer is a plane.

In the exit layer 1c, the amount of the phosphor in the direction vertical to the base plane may not depend on the position on the bottom surface, at least in the overlapping area 2233. Alternatively, the amount of the phosphor in the direction vertical to the base plane may vary with the period, in which the unit cells are arranged.

Some embodiments of the invention comprise a controller in order to control the LEDs. The first LEDs 2c and the second LEDs 3c may be controlled separately. That is, for example, for spectrum illumination, only the first LEDs 2c of all the unit cells illuminate the bottom surface of the exit layer 1c, while in white light illumination, only the second LEDs 3c illuminate the bottom surface of the exit layer. In an optional third mode, both the first LEDs 2c and the third LEDs 3c may illuminate the bottom surface of the exit layer. Controlling includes switching on and off, but may include other operations such as varying the light intensity, too. In addition, in some examples, specific ones of the first LEDs 2c and/or specific ones of the second LEDs 3c may be controlled separately.

FIGS. 12 to 18 show variations of the basic concept shown in FIG. 11. If not otherwise described, the properties explained with respect to the basic concept of FIG. 11 apply to FIGS. 12 to 18 correspondingly. Substantially, only the differences to the concept of FIG. 11 are explained hereinafter.

FIG. 12 shows a cross-section through an illumination apparatus according to some embodiments of the invention, and FIG. 13 shows a corresponding plan view. As may be seen from the cross-section of FIG. 13, the LEDs 2d and 3d forming one unit cell are arranged in a circle. From a conceptual point of view, in FIG. 13, the left and the right ends of the unit cells 23c are joined. Correspondingly, the exit layer 1d has an annual shape having the same center as the virtual circle, on which the LEDs 2d and 3d are placed.

In the variation of FIG. 14, the exit layer 1e has an annual shape, as in FIGS. 12 and 13, but in the cross-section, at least one of the bottom surface and the top surface is curved. In the example of FIG. 14, both the top surface and the bottom surface are curved. Thus, the exit layer may act like a lens in order to direct the light from the LEDs 2e and 3e and the respective converted lights into a desired direction. The plan view on the illumination apparatus of FIG. 14 corresponds to that of FIG. 13.

Figure 21:
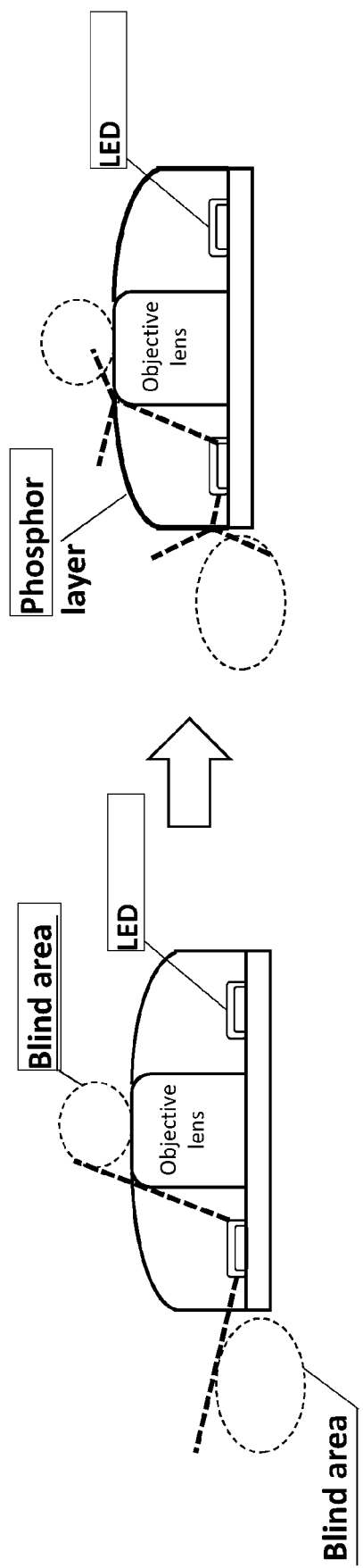
FIG. 21 illustrates how the blind area is reduced according to some embodiments of the invention.

Forming the exit layer in a lens shape has a particular advantage if the objective lens of the endoscope is arranged such that it is surrounded by the illumination apparatus of FIG. 14. Preferably, the optical axis of the objective lens coincides with the centerline of the illumination apparatus. If the objective lens has a wide field of view (such as in the order of 180° or even more, such as 225° or more), the lens shape of the exit layer enables illumination in a wide solid angle. In addition, the phosphor in the exit layer acts as a scattering center. Thus, the exit layer may act as a light diffuser, such that even the field of view beyond 180° may be sufficiently illuminated by the illumination apparatus surrounding the objective lens. That is, the blind area besides the tip of the endoscope shown in FIG. 2 may be reduced or even eliminated. By the same effect of light diffusion, also the blind area in front of the objective lens shown in FIG. 2 may be reduced. This is illustrated in FIG. 21, which repeats on the left side the prior art configuration of FIG. 2, and shows on the right side an illumination apparatus according to some embodiments of the invention, arranged around an objective lens.

FIG. 15 shows still another variation of the illumination apparatuses of FIGS. 11, 12, and 14. In the illumination apparatus according to FIG. 15, the first LEDs 2f and the second LEDs 3f are arranged at different levels with respect to the base plane. In the example of FIG. 15, the base plane is defined by the light-emitting faces of the first LEDs 2f, and the light-emitting faces of the second LEDs 3f are spaced apart from this plane by a distance d>0. The plan view on the illumination apparatus of FIG. 15 corresponds to that of FIG. 13.

FIG. 16 shows still another modification of the illumination apparatuses according to FIGS. 11, 12, 14, and 15. In the embodiment of FIG. 16, the first LEDs 2g and the second LEDs 3g of each units cell are arranged on circles having different radii. The first LEDs 2g are arranged on a circle with radius r1 around a centerline, and the second LEDs 3g are arranged on a circle with radius r2 around a centerline. r1 and r2 are different from each other. The exit layer 1g is arranged in an annual form having the same centerline as the circles, on which the first LEDs and the second LEDs are arranged. A plan view on the illumination apparatus of FIG. 16 is shown in FIG. 17.

Figure 18:
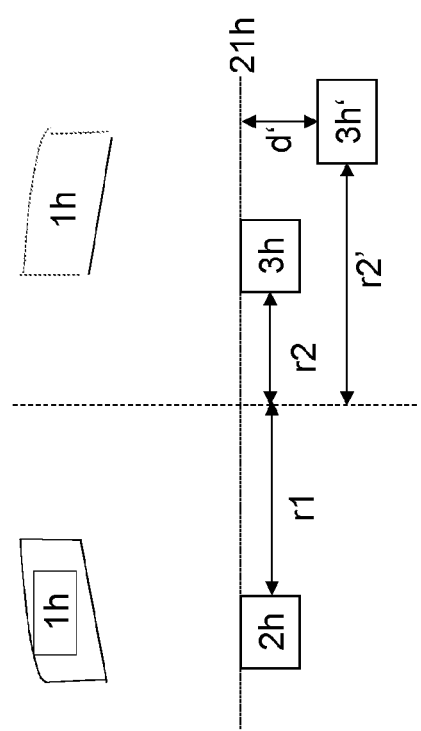
FIG. 18 shows a cross-section through an illumination apparatus according to some embodiments of the invention.

The variations shown in FIGS. 12, 14, 15, and 16 may be arbitrarily combined. An example of such a combination is shown in FIG. 18, which shows a cross-section of an illumination apparatus according to some embodiments of the invention. In this embodiment, the exit layer 1h has an annual shape around the centerline, and in the cross-section, the top surface and/or the bottom surface of the exit layer 1h is curved, similar to FIG. 14. Furthermore, the first LEDs 2h and the second LEDs 3h are arranged on circles around the centerline having different radii r1 and r2. In the example of FIG. 18, the unit cell comprises more than two LEDs. In addition to the first LED 2h and the second LED 3h, it comprises a third LED 3h'. The third LED 3h' may be of the second type (of the same type as the second LED 3h), or it may be of another type emitting a spectrum which is different from both of the first type and the second type.

This third LED 3h' is arranged on a third circle around the centerline, having a radius R2'. In addition, the third LED 3h' is arranged at an elevated level compared to the baseline 21h. In this example, the baseline 21h is defined by the emission faces of the first and second LEDs 2h and 3h.

FIG. 18 shows just one example of a combination of the different variations shown in FIGS. 12 to 17. Other combinations of such variations are within the scope of the present invention, too.

Figure 19:
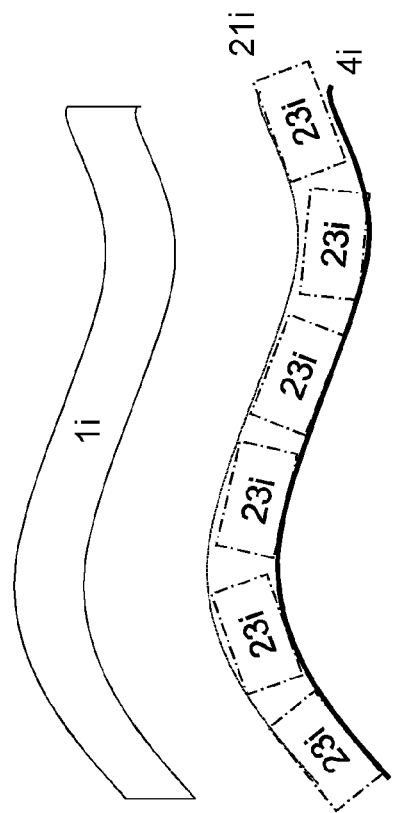
FIG. 19 shows a cross-section through an illumination apparatus according to some embodiments of the invention.

FIG. 19 shows another embodiment of the invention, which is still another variation of the embodiment of FIG. 11. In FIGS. 11 to 18, the unit cells are arranged along a base plane. A base plane is an example of a base area. In general, the base area may be curved. In the example of FIG. 19, the base area is curved because the unit cells 23i are arranged on a curved support layer 4i. The base area 21i is defined such that it connects corresponding positions at the top end of each of the unit cells 23i. However, it may be defined by connecting other corresponding points. Therefore, the support layer 4i may be considered as the base area, too. Each of the unit cells 23i comprises at least one first LED and at least one second LED.

Preferably, if the base layer is curved, the exit layer is curved correspondingly to the base layer, as shown in FIG. 19 (curved exit layer 1i).

FIGS. 30 and 31 show an embodiment of the invention, where the base layer 21k is a plane and the exit layer 1k has a curved cross-section. FIG. 30 shows a plane view on the base layer 21k, and FIG. 31 shows a cross-section through the base layer 21k and the exit layer 1k.

In detail, if the types of the LED are neglected, the first and second LEDs 2k and 3k are arranged symmetrically on both sides of a central line. On each side of the central line, the first and second LEDs 2k and 3k alternate. Each first LED 2k opposes a respective second LED 3k via the central line. Thus, two first LEDs 2k and two second LEDs 3k form a unit cell 23k.

The exit layer 1k comprising the phosphor is shaped in an arc (e.g. a circular arc) above the base layer 21k. An apex of the arc of the exit layer 1k is arranged such that it coincides with the central line in the plan view. The exit layer 1k extends in the direction of the central line. The exit layer 1k is symmetrical around a symmetry plane comprising the central line and the apex of the exit layer 1k.

If the distance between the base layer and a center line of the bottom surface of the exit layer 1k intersecting with the symmetry plane is sufficiently large, the first LEDs 2k and the second LEDs 3k may illuminate the center line of the bottom surface of the exit layer 1k substantially homogeneously. E.g., a variation of a total intensity of the first light from the first LEDs 2k may be less than 20%, and a variation of a total intensity of the second light from the second LEDs 3k may be less than 20%.

FIGS. 30 and 31 show an illumination unit, wherein the unit cells 23k are arranged linearly along the central line, and the exit layer extends linearly in the same direction. Instead of this linear arrangement, in some embodiments of the invention, the unit cells 23k are arranged in a curve (e.g. a circle) and the exit layer extends in a corresponding curve (e.g. a circle).

In order to ensure "relatively homogeneous" illumination, each position of a particular line (such as a center line) on the bottom surface of the exit layer should be illuminated by all the LEDs of at least one unit cell. The definition of a unit cell may depend on the position on the particular line of the bottom surface of the exit layer. Furthermore, each position of the particular line on the bottom surface should be illuminated by corresponding LEDs of at least two unit cells.

Figure 20:
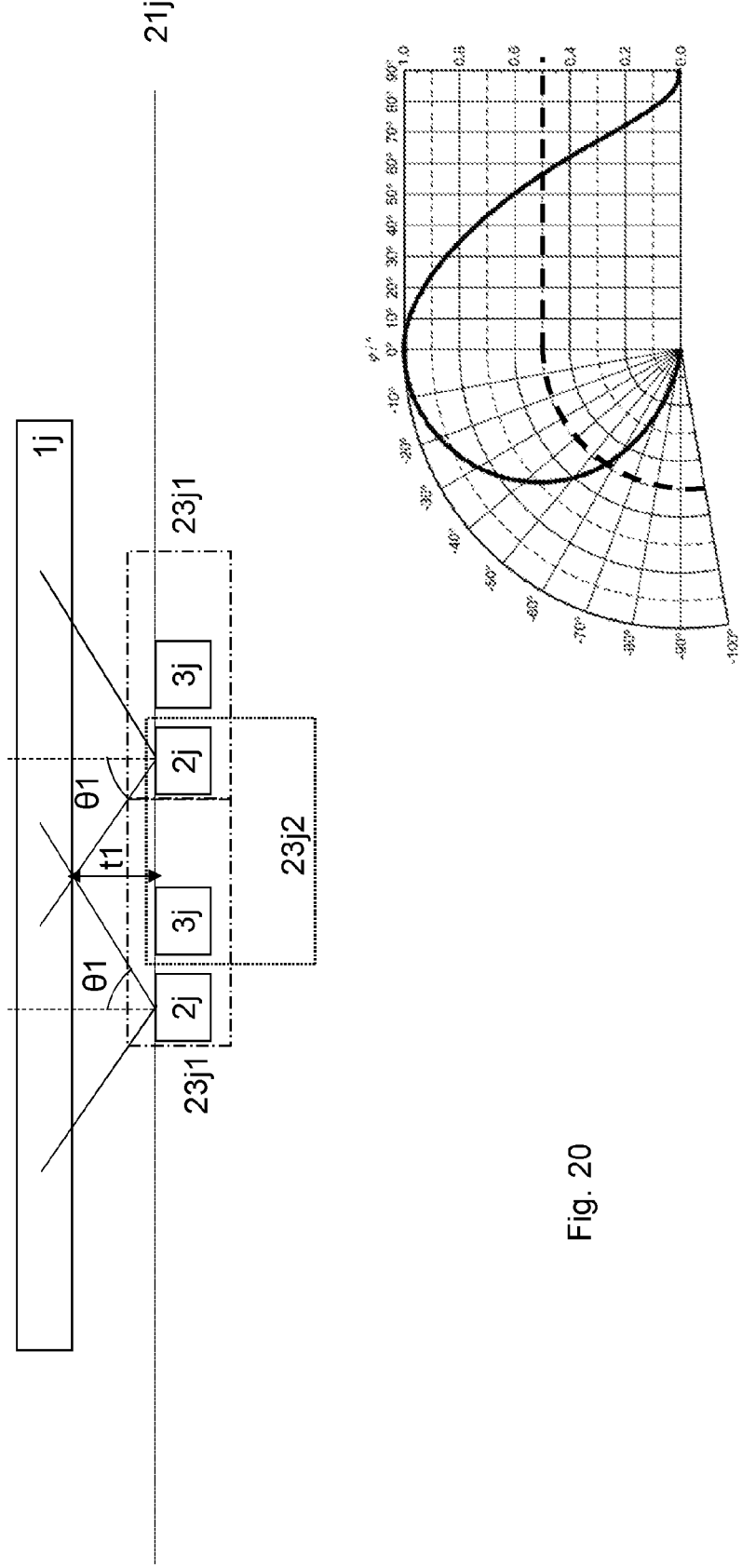
FIG. 20 illustrates how a minimum distance between the light sources and the exit layer may be calculated.

FIG. 20 illustrates a minimum distance which the exit layer should have from the light emission surfaces of the LEDs for a case that the light emission surfaces of the LEDs are arranged in a line below the particular line of the exit layer. I.e, FIG. 20 corresponds to a section of FIG. 11. Two adjacent unit cells 23j each comprising a LED 2j and a LED 3j of a different type are shown in FIG. 20.

In FIG. 20, the minimum distance is derived for the LEDs 2j. In order to ensure that each position on the particular line of the bottom surface of the exit layer 1j is illuminated by at least one LED 2j with its half maximum radiation power, the minimum distance t1 is $$t1 \geq \frac{r1}{2*\tan\theta 1}$$

where r1 denotes the distance between corresponding LEDs of each of the unit cells 23j1, and θ1 denotes the angle of half maximum radiation power in the radiation pattern characteristics of each LED 2j. The box 23j2 denotes another possible definition of a unit cell equivalent to the definition of the unit cells 23j1. An example radiation pattern is shown on the bottom of FIG. 20.

However, since the LEDs 2j and 3j are arranged in unit cells 23j, and the arrangement of the LEDs is the same in each of the unit cells 23j, the same consideration applies to the LEDs 3j. If the LEDs have different distances to the particular line of the bottom surface of the exit layer (such as in FIGS. 15 and 18), a minimum distance may be derived correspondingly for each of the LED types, and the largest of these minimum distances should apply.

Preferably, each position on the bottom surface of the exit layer is illuminated by the LEDs of at least one unit cell with their respective half maximum radiation power. Furthermore, each position on the bottom surface of the exit layer is preferably illuminated by the corresponding LEDs of at least two unit cells.

In a typical arrangement, the distance between the LEDs and the bottom surface of the exit layer may be between 1 mm and 10 mm, preferably between 3 mm and 8 mm.

The LEDs of one type (first LEDs, second LEDs) have a same spectrum. If they have different maximum radiation powers, the half maximum radiation power discussed hereinabove may be replaced by a fixed value lower than a maximum radiation power of the LED with the smallest maximum radiation power.

FIGS. 22 to 27 illustrate examples, how the illumination apparatus according to some embodiments of the invention may be operated together with an image sensor for capturing an image of the scene illuminated by the illumination apparatus.

Figure 22:
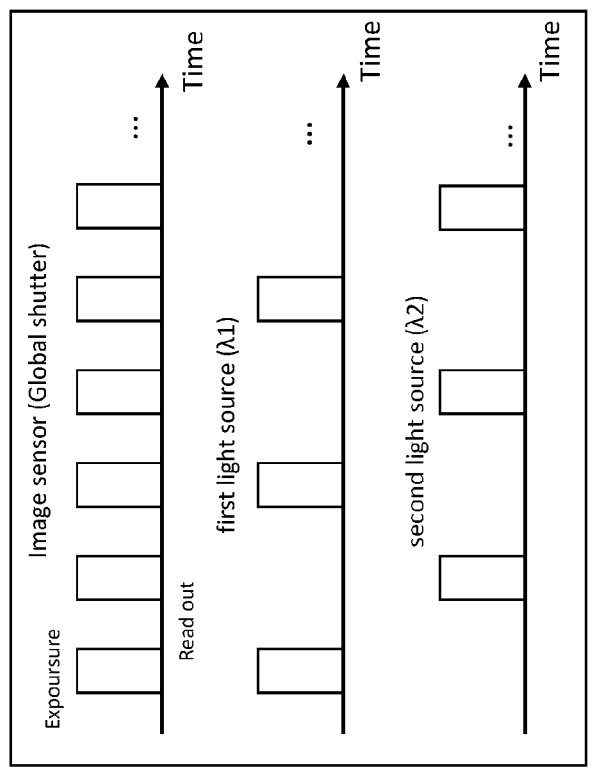
FIG. 22 illustrates a timing diagram of operating an illumination apparatus according to some embodiments of the invention.
Figure 23:
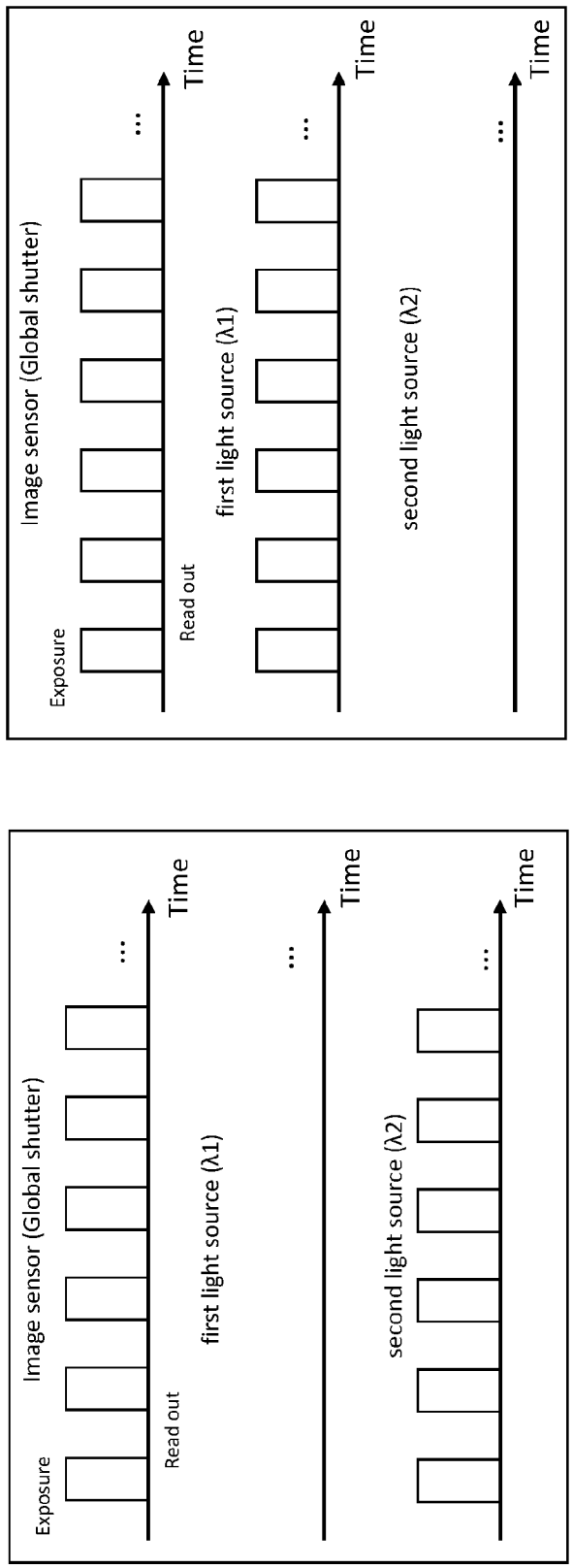
FIG. 23 illustrates another timing diagram of operating an illumination apparatus according to some embodiments of the invention.
Figure 24:
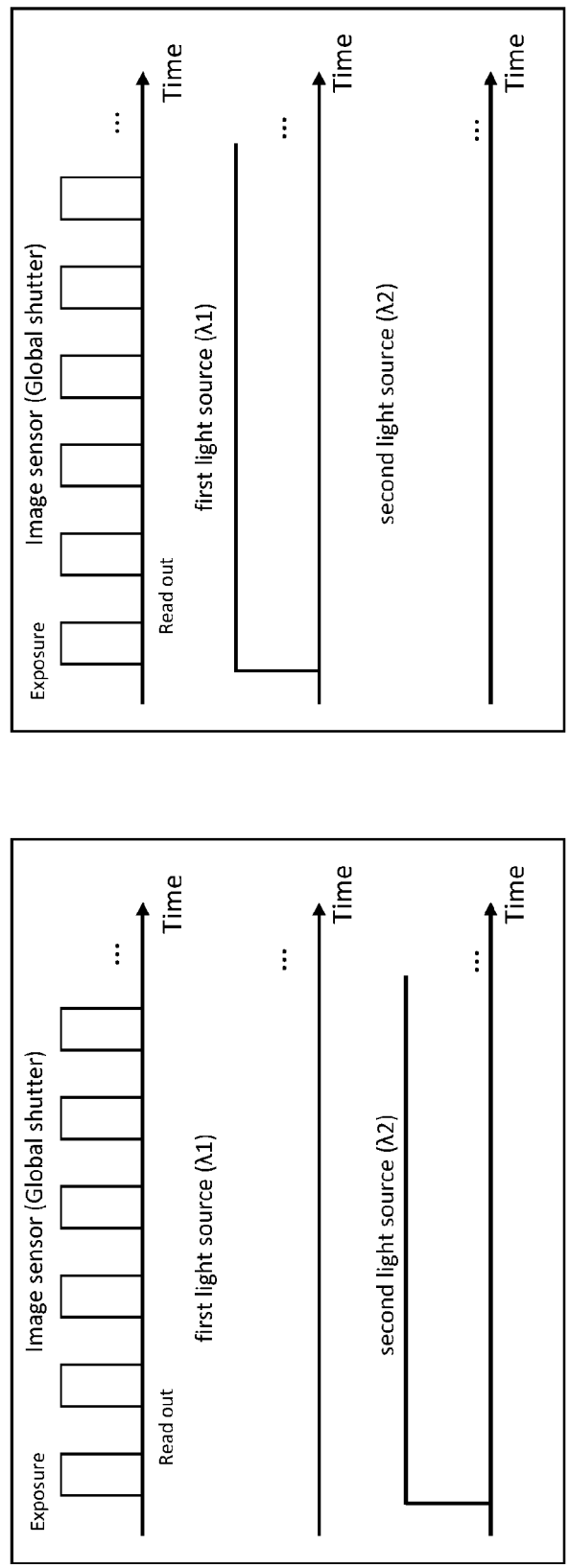
FIG. 24 illustrates a timing diagram of operating an illumination apparatus according to some embodiments of the invention.
Figure 25:
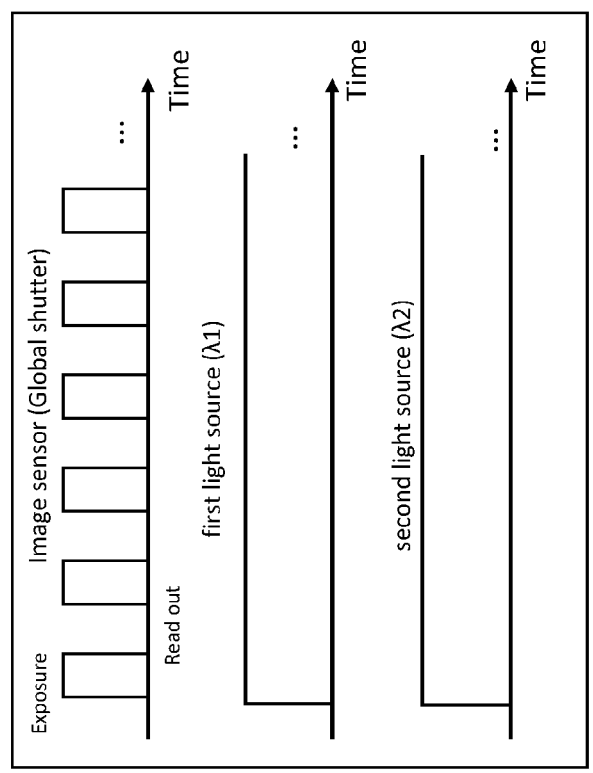
FIG. 25 illustrates another timing diagram of operating an illumination apparatus according to some embodiments of the invention.

According to FIG. 22, the first and second light sources (e.g. LEDs of different emission wavelengths) are alternately switched on, basically synchronous with the exposure time of the image sensor. According to FIG. 23, only one of the light sources is switched on basically synchronous with the exposure time of the image sensor, while the other of the light sources is kept switched off. After a certain time, the first and second light sources may switch their roles. According to FIG. 24, one of the light sources is permanently switched on (i.e., even during the readout time of the image sensor. The other light source is permanently switched off. As in FIG. 23, after some time, the first and second light sources may switch their roles. FIG. 25 corresponds to FIG. 24, but here, both light sources are permanently switched on. Thus, the scene may be illuminated with a spectrum different from those obtained according to FIGS. 22 to 24.

Figure 27:
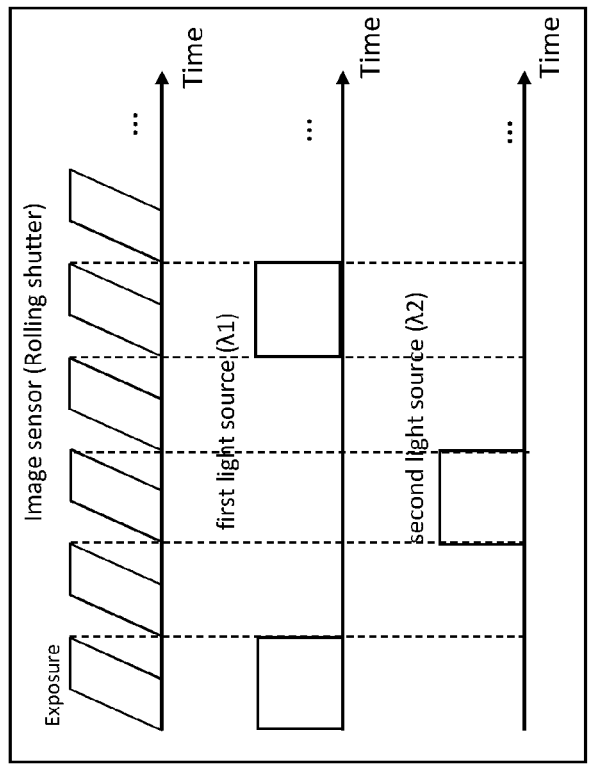
FIG. 27 illustrates another timing diagram of operating an illumination apparatus according to some embodiments of the invention.
Figure 26:
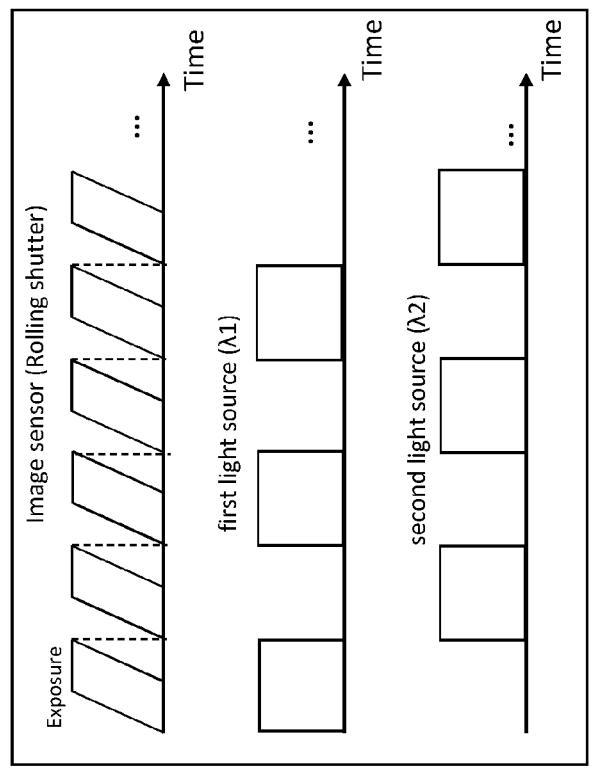
FIG. 26 illustrates another timing diagram of operating an illumination apparatus according to some embodiments of the invention.

In the examples of FIGS. 26 and 27, the image sensor is exposed by a rolling shutter, wherein only a part of the image sensor is exposed at a time, and this part is shifted (rolls) over the sensor area. According to FIG. 26, for each sweep of the rolling shutter, one of the two light sources illuminates the exit layer while the other light source is dark. The light sources are alternately switched on and off. Thus, images may be taken at a higher speed than according to FIG. 27, wherein a dark sweep, where none of the light sources is switched on, is inserted between two illuminations by different light sources. The illumination scheme of FIG. 27 corresponds to the illumination scheme of FIG. 22. The rolling shutter may be applied to the illumination sequences of FIGS. 23 to 25, too.

FIGS. 28 and 29 show example illumination spectra if the phosphor in the exit layer is a mixed phosphor (e.g. a nitride and/or $CaAlSiN_3$ (CASN), and/or $(Sr,Ca)AlSiN_3$ (SCASN)). In FIG. 28, the illumination spectrum for white light illumination is shown, which has peaks at λ1 and λ2 (the emission wavelengths of the white LED) and an additional broad maximum at a larger wavelength λ4 (e.g. 675 nm). For example for near infrared imaging and/or near infrared photoimmunotherapy, a light source (LED) emitting at a peak wavelength of λ4 may be selected. Thus, the spectrum comprises nearly only one broad peak around λ4 (and another smaller peak at λ3 at a higher wavelength, due to some spectrum from the light source).

Some embodiments of the invention solve still a further problem in spectrum imaging. In a conventional endoscope, the distal tip portion may comprise an infrared LED and a white LED, wherein the white LED comprises a violet (UV) LED and a phosphor excited by the light from the violet LED. The phosphor covers the violet LED. In such a conventional distal tip portion, the phosphor of the white LED may be excited by violet light components emitted by the infrared LED and reflected by members of the endoscope. This spectrum portion from the phosphor of the white LED may be received as noise in spectrum imaging. The problem is particularly relevant in case a phosphor with a high efficiency for violet light (such as CASN or SCASN) is used for the white LED.

In contrast to the conventional endoscope, in some embodiments of the invention, the exit layer is arranged between the white LED and the object to be illuminated. If the phosphor in the exit layer generates violet light, only a small portion will hit the white LED, and an even smaller portion of the light from this phosphor will pass to and through the exit layer. Hence, noise is reduced. As another option, in some embodiments of the invention, the phosphor to generate white light may not cover the violet LED but may be present in the exit layer only. If this phosphor is provided on the side of the exit layer towards the LEDs, its contribution to the illumination of the object may be reduced, too.

Of course, this effect is not limited to the above combination of an infrared LED and a white LED and it may be achieved for other combinations, too, where the phosphor of one LED may be excited by light from the other LED reflected from members of the endoscope.

The present invention is described with LEDs as light sources. However, instead of an LED, an emission end of an optical fiber may be used. In this case, the input end of the optical fiber is connected to an emission light source emitting the respective light. More in detail, in case the optical fiber changes the spectrum of the light passing through the optical fiber, the emission light source has to compensate for this change of spectrum. The optical fibers of the light sources of the same type may be connected to a single emission light source, or some of them may be connected to separate emission light sources. Example of emission light sources are LEDs and lasers. In the case of optical fibers, the controller controlling the emission of the first lights and second lights may control the emission of the emission light source or may control the shutter enabling or disabling the transmission of the light from the emission light source to the emission end of the optical fiber.

In the FIGS. 11 to 19, the unit cells are arranged one-dimensionally, for example in a line or in a circle. However, in some example embodiments of the invention, the unit cells may be arranged two-dimensionally, for example in a rectangular grid, a square grid, or a hexagonal grid.

The shape of the exit layer may preferably correspond to the arrangement of the unit cells, but it may differ from this arrangement.

As explained hereinabove, the illumination apparatus is preferably arranged in a rigid tip of an endoscope for inserting into a lumen of the human body. Such a rigid tip may comprise an objective lens, and the illumination apparatus may be arranged around the objective lens. Furthermore, the rigid tip may comprise an image sensor, a working channel, etc. The rigid tip may be connected with a flexible tube such that embodiments of the invention also encompass an endoscope. In some embodiments, the rigid tip may be used stand-alone (i.e., without being connected to a flexible tube of an endoscope). Thus, the illumination apparatus may be employed in so called "capsule endoscopy".

The invention claimed is:

1. Illumination apparatus, comprising
an exit layer comprising a bottom surface and a top surface opposite to the bottom surface, wherein a phosphor is arranged in the exit layer;
a plurality of first light sources, each configured to emit, from a respective light emitting face, a first light of a first emission spectrum;
a plurality of second light sources, each configured to emit, from a respective light emitting face, a second light of a second emission spectrum different from the first emission spectrum; wherein,
the first light sources and the second light sources are arranged in plural unit cells;
each of the unit cells comprises at least one of the first light sources and at least one of the second light sources;
in each of the unit cells, the respective at least one first light source and the respective at least one second light source are arranged in a same way;
the plurality of unit cells is arranged periodically with a first period in a base area;
the plurality of the first light sources is controllable separately from the plurality of the second light sources;
the first and second light sources are arranged spaced apart from the exit layer such that, if the first and second light sources emit the first and second lights, respectively, each position of the bottom surface is illuminated by first lights from first light sources of at least two of the unit cells and by second lights from second light sources of at least two of the unit cells;
the phosphor is configured to convert at least a portion of the first lights into first converted lights such that, if the first and second light sources emit the first and second lights, a combined light exits the top surface of the exit layer;
if the phosphor is configured to convert at least a portion of the second lights into second converted light, the combined light comprises remaining portions of the first lights, remaining portions of the second lights, the first converted lights, and the second converted lights, wherein a spectrum of the first converted lights is different from a spectrum of the second converted lights;
if the phosphor is not configured to convert at least a portion of the second lights into second converted light, the combined light comprises remaining portions of the first lights, the second lights, and the first converted lights;

if the first and second light sources emit the first and second lights, respectively, on a line connecting corresponding positions of two adjacent unit cells of the plurality of unit cells projected on the bottom surface, a variation of a total intensity of the first lights is less than 20%, and a variation of a total intensity of the second lights is less than 20%.

2. The illumination apparatus according to claim 1, wherein, within each of the unit cells:

the light emission faces of all of the first light sources and the light emission faces of all of the second light sources of the respective unit cell are arranged in the base area; or the light emission face of at least one of the first light sources and the second light sources of the respective unit cell is arranged in an elevated area different from the base area, and the light emission faces of the remaining first light sources and the light emission faces of the remaining second light sources of the respective unit cell are arranged in the base area.

3. The illumination apparatus according to claim 1, wherein, an amount of the phosphor in a direction perpendicular to the base area is independent from a position on the bottom surface or modulates with the first period depending on the position on the bottom surface.

4. The illumination apparatus according to claim 1, wherein at least one of either each of the first light sources is a respective LED, or each of the first light sources is an emission end of a respective optical fiber connected at its input end to an emission light source of the respective first light;

either each of the second light sources is a respective LED, or each of the second light sources is an emission end of a respective optical fiber connected at its input end to an emission light source of the respective second light.

5. The illumination apparatus according to claim 1, wherein the emission of the first lights by the first light sources and the emission of the second lights by the second light sources are separately controllable.

6. The illumination apparatus according to claim 1, wherein, either the unit cells are arranged in the base area one-dimensionally with the first period, or the unit cells are arranged in the base area in a first dimension with the first period and in a second dimension with a second period.

7. The illumination apparatus according to claim 6, wherein the unit cells are arranged one-dimensionally in a circle, and the first period is an angular period.

8. The illumination apparatus according to claim 7, wherein the exit layer acts as a light diffuser such that the combined light exits the exit layer in an angle of more than 180° around a center of the circle.

9. A rigid tip of an endoscope or a capsule endoscope for inserting into a lumen of a human body, comprising an objective lens and the illumination apparatus according to claim 7 arranged around the objective lens.

10. An endoscope comprising a rigid tip according to claim 9, wherein the rigid tip is connectable to a flexible tube.

* * * * *